(12) United States Patent
Bennett (10) Patent No.: US 7,335,176 B2
(45) Date of Patent: Feb. 26, 2008

(54) DIGIT-SUPPORTING THERAPEUTIC DEVICE FOR THE HAND

(76) Inventor: Marc Bennett, 6404 N. Richmond #205, Chicago, IL (US) 60645

( * ) Notice: Subject to any disclaimer, the term of this patent is extended or adjusted under 35 U.S.C. 154(b) by 148 days.

(21) Appl. No.: 11/111,633

(22) Filed: Apr. 21, 2005

(65) Prior Publication Data

US 2005/0197610 A1   Sep. 8, 2005

Related U.S. Application Data

(63) Continuation of application No. 10/389,079, filed on Mar. 17, 2003, now Pat. No. 6,887,212.

(51) Int. Cl.
*A61F 5/00* (2006.01)
(52) U.S. Cl. ............................ 602/20; 602/22; 128/878
(58) Field of Classification Search ............ 602/20–23, 602/63, 64; 2/161.1, 161.2, 161.3, 161.4; 128/878–880; 441/57–58
See application file for complete search history.

(56) References Cited

U.S. PATENT DOCUMENTS 3,707,730 A * 1/1973 Slider ......................... 2/161.1
4,618,328 A * 10/1986 Chi ............................. 441/57
4,964,824 A * 10/1990 Spencer et al. ............... 441/57
5,762,621 A * 6/1998 Schultz ........................ 602/64
5,848,440 A * 12/1998 Pajarola ...................... 2/161.1
6,013,044 A * 1/2000 Estwanik ..................... 602/64
6,179,751 B1 * 1/2001 Clears ......................... 482/48

* cited by examiner

*Primary Examiner*—Michael A. Brown
(74) *Attorney, Agent, or Firm*—Milton S. Gerstein (57) ABSTRACT

A therapeutic hand device comprising a first thumb-sleeve for receiving therein the thumb of a hand, a second index-finger sleeve for receiving therein the index finger of the hand, and a third middle-finger sleeve for receiving therein the middle finger of the hand. The first thumb-sleeve is connected to said second sleeve and is also connected to the third sleeve by adjustable straps. An open space is defined interiorly of, and delimited by, the first, second and third sleeves, whereby when the device is worn on a hand, an object may be inserted into the open space between the first, second and third sleeves, with the adjustable straps being used to firmly hold the thumb and fingers in a pincer hold against the object, whereby the object may be held and manipulated with support and assistance by the device.

14 Claims, 8 Drawing Sheets

DIGIT-SUPPORTING THERAPEUTIC DEVICE FOR THE HAND

CROSS-REFERENCE TO RELATED APPLICATION

The present application is a continuation of application Ser. No. 10/389,079, filed on Mar. 17, 2003, now U.S. Pat. No. 6,887,212.

BACKGROUND OF THE INVENTION

The present invention is directed a therapeutic device for the hand and for assisting a person in holding and gripping objects. The apparatus of the invention is a hand-worn or fingers-worn device made to give total or partial support to the fingers of hand while using tools, and similar hand-carried and manipulatable items. The device of the invention supports the fingers of the hand in their functional positions, with the thumb able to oppose the fingers in either fixed or other desired positions.

Support devices for the hand are well-known. Examples of such are golf gloves, bowler's gloves, and the like. Some prior-art supports for the hand are therapeutic, by helping to support the hand, or one or more digits. Examples of prior-art therapeutic support devices for the hand are shown in the U.S. Pat. Nos. 3,152,337; 4,953,568; 5,762,621; 6,029,277; and 6,095,994. However, prior-art therapeutic hand-devices are either directed to treating a specific problem, or are cumbersome and bulky in use, preventing the digits from easily holding and manipulating a tool or object while at the same time providing the therapeutic support and treatment required.

SUMMARY OF THE INVENTION

It is, therefore, the primary objective of the present invention to provide a therapeutic device for the digits of a hand that allows the fingers of the hand to hold, use and manipulate an object, tool, and the like, while at the same time providing therapeutic support thereto.

It is a primary objective of the present invention to provide such a therapeutic device for the digits of a hand which allows the fingers or hand to hold, use and manipulate an object, tool, and the like, while at the same time providing therapeutic support thereto, which device therapeutically supports at least the thumb, index finger and middle finger, such that the index and middle fingers are held in opposition to the thumb.

The therapeutic hand device of the invention provides support to the fingers while performing a variety of pinches, including; tripod pinch, key pinch, and pincer. It provides gradable support by, for example, placing the finger-sleeves closer to the distal intercarpophalangeal (DIP) joint, distally closer to the intercarpophalangeal (IP) joint, or proximally closer to the metacarpophalangeal (MP) joint. Support straps may be adjustable to fasten the device to give more or less support, or may use tightly fitting stretchable material for straps.

The occupational therapy device of the present invention offers gradable or variably-adjustable support to the thumb and index and middle fingers of the hand as it is used during routine activities, such as for holding a pencil, screwdriver, and the like, and consists of, in the preferred embodiment, three interconnected flexible sleeves: A first thumb-sleeve in which a thumb is received, a second sleeve in which the index finger is received, and a third sleeve in which the middle finger is received. The device is made of flexible and stretchable fabric, and defines an interior opening or hollow volume delimited and bounded by the three sleeves, in which volume an object or tool may be inserted to be held for use. The flexible and stretchable nature of the sleeves provides an adjustable and variable support or force; that is, as the thumb and two fingers are pulled away from other other, a greater biasing force is provided to thus help the thumb and fingers support an object or tool positioned in the volume between the sleeves. In order to allow the therapeutic device of the invention to fit variously-sized hands, the interconnection between the three sleeves may be achieved by means of adjustable bands or cords, the effective lengths of which may be varied.

In alternative embodiments, the therapeutic device of the invention has additional finger-supporting sleeves for other fingers besides the index finger and middle finger, and may also be provided as part of an overall glove-type device or wrist-support element.

The present invention provides an occupational-therapy device that is more effective, safer, and allows a multitude of different tools to be used hitherto not possible with any glove or hand support. This new hand support or glove utilizes a simple, yet effective, method of configuring and supporting the fingers of the hand while using virtually any type of hand tool. Some examples of hand tools it assists the hand to use are: a pen, spoon, fork, or knife, cell phone, screwdriver, electric or safely razors, power tools, baby bottles, cups or glasses, hair brushes or combs, knitting or crotchet needles, kitchen tools, golf clubs and tennis rackets.

The finger-support system of the invention may be included as part of a type of glove or wrist-support. The glove is made with five finger-sleeves or pieces. The finger-sleeves may be sewn together either partially or completely. A strategically placed slit is made on each sleeve for a corresponding, adjustable strap approximately one quarter inch wide. The straps are attached to the thumb piece at one end. The other ends are slid through the slits on the finger-sleeves. These straps are preferably approximately three to four inches long, and attach to themselves, or to the back of, the thumb with "VELCRO". The straps are attached on each side of the thumb, and will attach the thumb to the first and second fingers, in a position known in the field of occupational therapy as the tripod pinch. When moving the fingers away from the thumb, there is a space or volume therebetween through which an object may be placed to be held and used. The straps may be tightened or loosened, to adjust to the size or type of tool being used, and then re-tightened for support of the hand while using the desired tool. With the straps in their longest position, the hand is in the functional position. A wrist support strap may also be added, if desired. The device of the invention supports the thumb while it opposes the other fingers. This is of paramount importance, as the thumb is what facilitates the use of tools and allows fine motor skills. The support given by the device of the invention allows the hand to require reduced force during tool use. It takes stress off of the hand and wrist, limits wrist range of motion, making it ideal for those who suffer from such conditions as carpal tunnel syndrome, arthritis, multiple sclerosis, fractures, strokes or brain injury, diabetic neuropathy, and many other neurological or orthopedic problems. It decreases wear and tear on wrist and finger structures, making it useful for anyone who uses his hands frequently with numerous types of hand tools. It also improves fine motor skills while supporting various 'pinches', while performing such tasks as turning a nut and bolt, sewing, needlepoint, and picking up small objects.

Total support can be given initially, and gradually decreased as one's skill and coordination improves.

BRIEF DESCRIPTION OF THE INVENTION

The invention will be more understood with reference to the accompanying drawing, wherein.

DETAILED DESCRIPTION OF THE INVENTION

Figure 3:
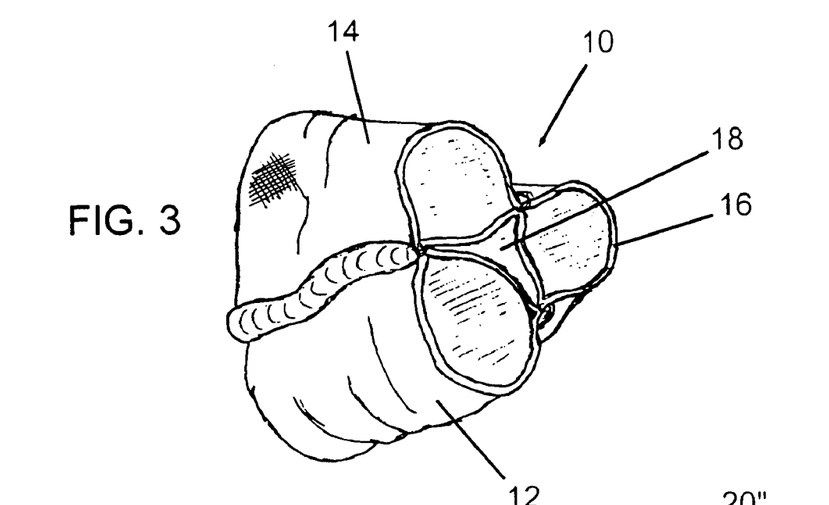
FIG. 3 is a top isometric view of the digit-supporting therapeutic device itself for the fingers of a hand of FIG. 1.

Referring now to the drawings in greater detail, and in particular to FIGS. 1-10, for now, there is shown the first embodiment of the digit-supporting therapeutic device for a hand of the invention. The device 10 consists of three separate sleeves: A first thumb-sleeve 12, an index-finger or forefinger-sleeve 14, and a middle-finger sleeve 16, as best seen in FIG. 3. Each sleeve is preferably made of a flexible and stretchable fabric or material, such as spandex, nylon, or the like, and are sewn, or otherwise fixedly secured together by connecting means for connecting along adjacent edge-surfaces or first and second connecting portions, as clearly seen in FIG. 3. The sleeves are arranged so as to allow the thumb-sleeve 12 to be positioned in opposition to the two finger-sleeves 14, 16 when the device 10 is worn on the fingers of a hand, in a manner depicted in FIGS. 1 and 2. The flexible stretchable nature of the sleeves allows the thumb to be separated from the combined two opposed fingers, such that, the greater the distance the thumb-sleeve is moved form the combined two opposed fingers, the greater the restoring biasing force, so that an object or tool inserted into an interior hollow volume or space 18 defined between the sleeves is held firmly between the thumb and two fingers in a pinching grip, or the like, for use.

Figure 4:
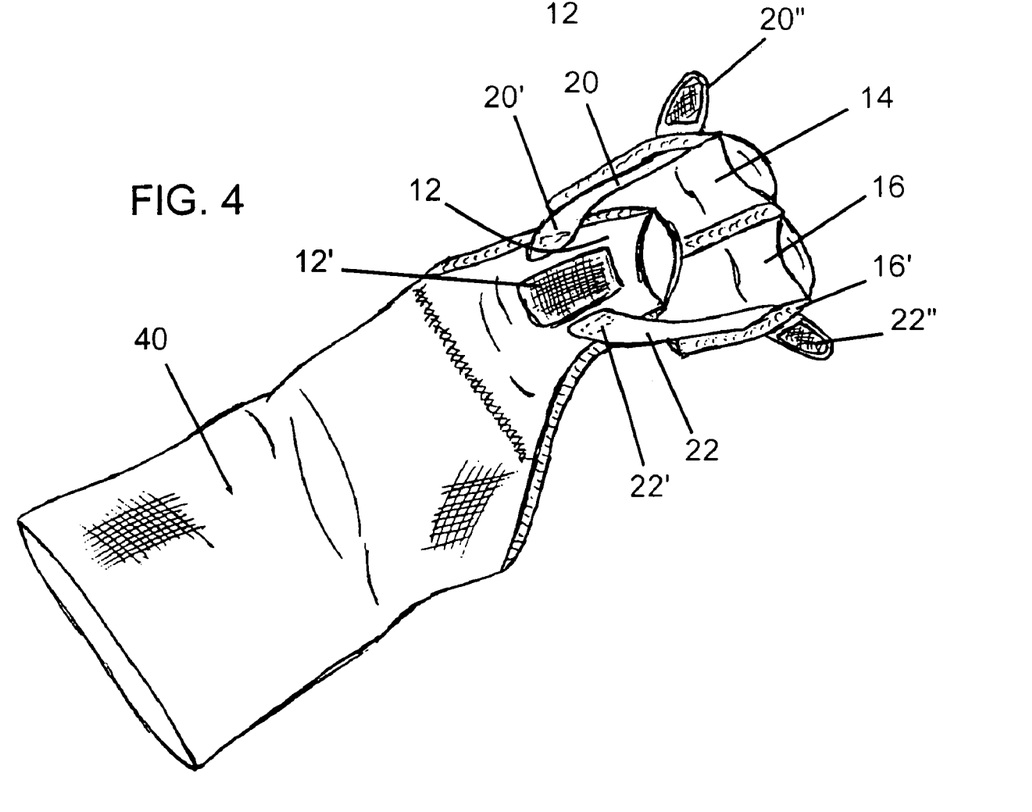
FIG. 4 is a front isometric view of a modification of the first embodiment of the digit-supporting therapeutic device for the hand according to the invention having adjustable sleeve-interconnecting bands or connectors, where a wrist support is provided to which is integrally formed the thumb-sleeve of the digit-supporting therapeutic device of FIG. 1.
Figures 5A, 5B:
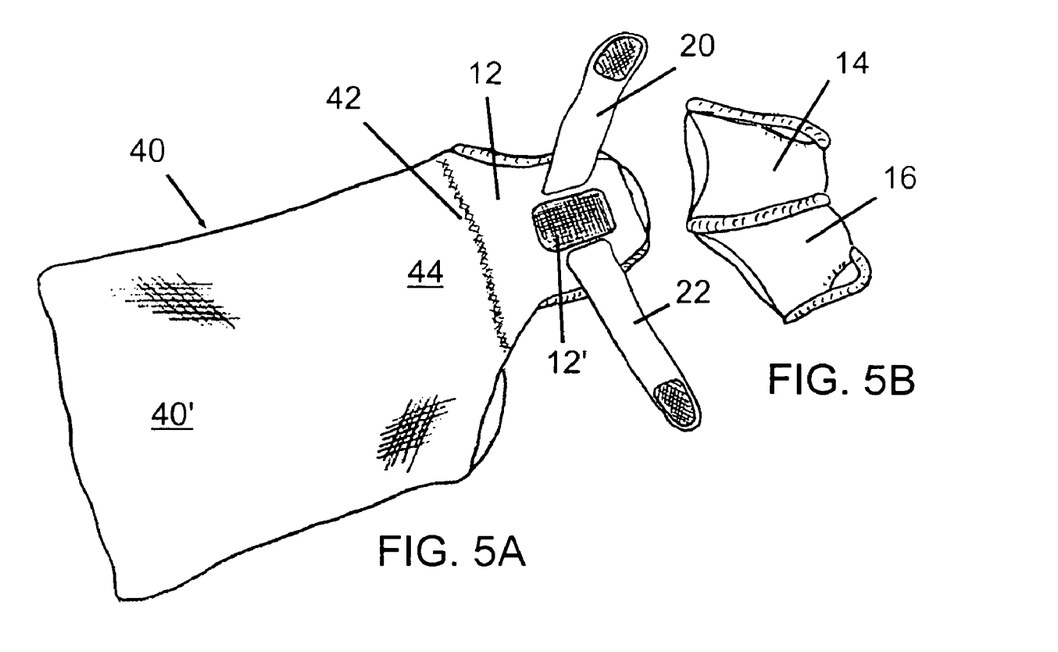
FIG. 5A is a top plan view thereof.
FIG. 5B is a plan view showing the separate interconnected finger-sleeves for this modification.
Figure 6:
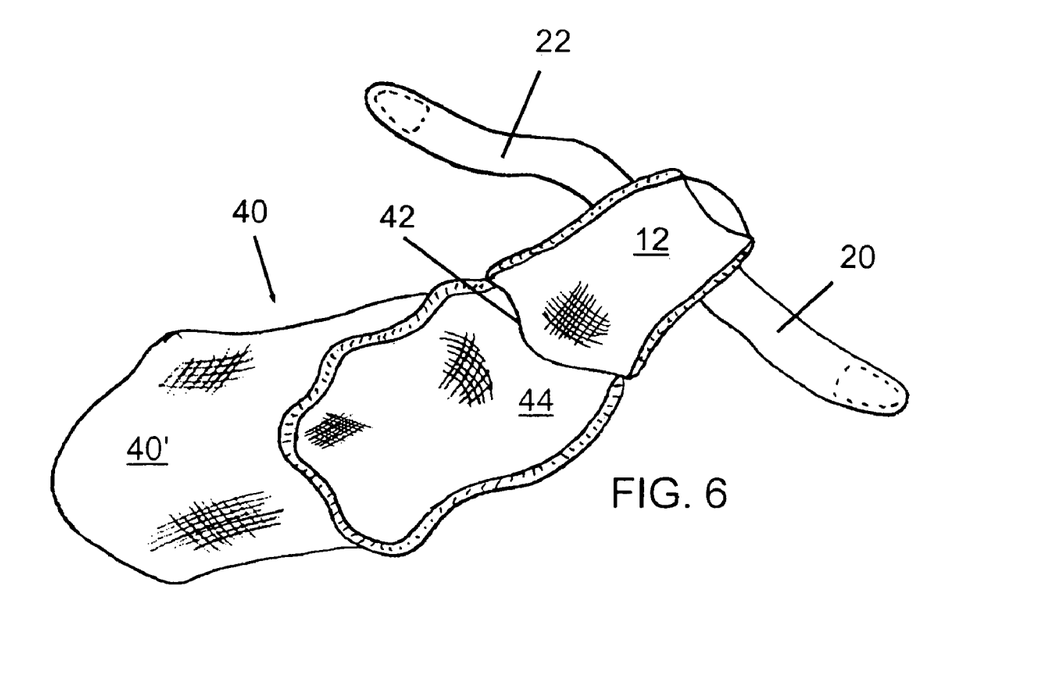
FIG. 6 is a bottom view thereof.

Instead of the finger-sleeves 14 and 16 being fixedly secured or attached to the thumb-sleeve 12, each sleeve 14, 16 may be attached to the thumb-sleeve by means of length-adjustable straps or bands 20 and 22, as best seen in FIGS. 4-6, in order to allow the device 12 to be fitted to hands of different sizes, and in order to allow initial pinching or gripping of an object in the space 18 and the later tightening thereof, as described hereinbelow. In this modification, the strap 20 has a first end 20' fixedly secured to an outer portion or surface of the thumb-sleeve 12, and second end 20" inserted through a slot or opening 14' formed in an outer surface portion of the first index-finger sleeve 14. Preferably, the outer or outwardly facing surface of the strap or band 20 is provided along most of its length with the first portion or half of a hook-and-pile fastener, while the outer or outwardly facing surface of the second end 20" is provided with the second portion or half of the hook-and-pile fastener, whereby the second end 20" may be removably attached to any portion along the length of the strap 20, to thereby vary the effective length of the strap 20 and the distance between the thumb-sleeve 12 and the index-finger sleeve 14. The strap 22 similarly has a first end 22' fixedly secured to an opposite outer portion or surface of the thumb-sleeve 12, and second end 22" which is inserted through a slot or opening 16' formed in an outer surface portion of the middle-finger sleeve 16. Preferably, the outer or outwardly facing surface of the strap or band 22 is provided along most of its length with the first portion or half of a hook-and-pile fastener, while the outer or outwardly facing surface of the second end 22" is provided with the second portion or half of the hook-and-pile fastener, whereby the second end 22" may be removably attached to any portion along the length of the strap 22, to thereby vary the effective length of the strap 22 and the distance between the thumb-sleeve 12 and the middle-finger sleeve 16. In this modification, the two finger-sleeves 14 and 16 are fixedly sewn, or otherwise secured together, along adjacent-facing surfaces as seen in FIGS. 4 and 5B. Moreover, a portion 12' of the thumb-sleeve on the surface thereof facing away from the two finger-sleeves 14, 16 is also provided with the a first half or portion of the hook-and-pile fastener 12", so that the second ends 20" and 22" may be removably fastened thereto after having passed through the slots 14', 16' (not shown in FIG. 5B) after the device 10 is worn and an object, tool, or the like, is placed in the hollow interior volume 18, whereby the thumb-sleeve 12 and the pair of juxtapositioned two adjacent finger-sleeves 14, 16 may be brought as close as possible together to firmly close and "lock" the sleeves against the object or tool being held in the hollow interior volume 18, so that the greatest amount of support is provided to the thumb and fingers for assisting the pinching or gripping the object, tool, and the like, in a manner depicted in FIG. 9, where the object shown is a pencil. When it is desired to release the object or tool, the second ends 20", 22" are simply unfastened, allowing the sleeves to separate and expand the volume 18, whereby the object or tool may be readily released and removed.

Figure 10:
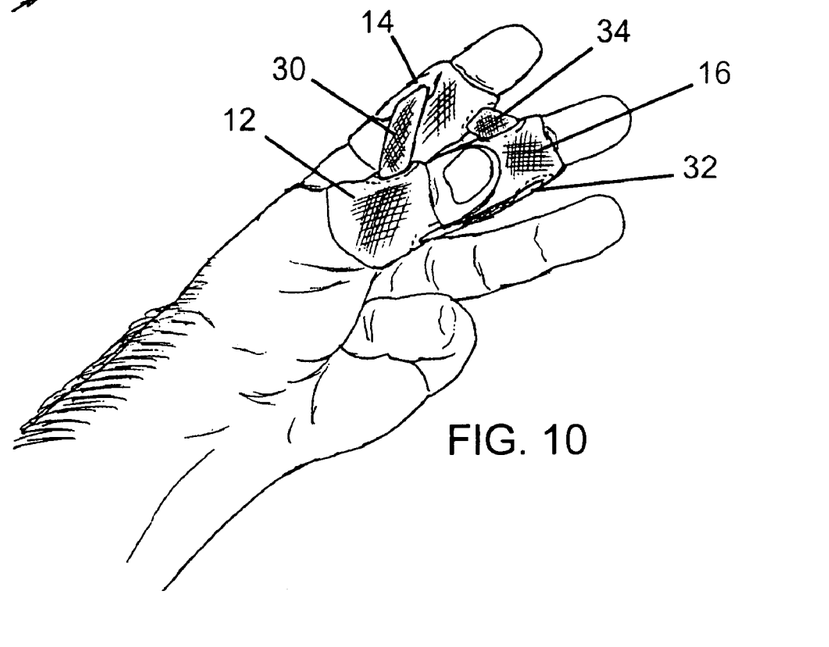
FIG. 10 is a front isometric view of another modification similar to that of FIG. 4 but using digit-supporting sleeves that are interconnected by flexible and stretchable straps or bands.

Alternatively, instead of the sleeves 12, 14, 16 being fixedly secured together or having the length-adjustable straps 20, 22, fixed flexible and stretchable straps 30, 32, and 34, as seen in FIG. 10, may be used. Each strap 30, 32, has one end fixedly secured to a respective finger-sleeve 14, 16 and a second end affixed to an opposing, juxtapositioned portion or section of the thumb-sleeve 12. The strap 34 is fixedly connected at its ends to, and interconnects with, the two finger-sleeves 14, 16. The flexible, stretchable nature of the straps 30 and 32 allow the device to fit various-sized hands, and inherently provides an ever-increasing biasing force for holding an object in the hollow volume 18 when the thumb-sleeve 12 is moved away from the pair of two finger-sleeves 14, 16 when an object or tool is inserted in the hollow volume 18. The use of these affixed stretchable straps 30, 32 provides a limited degree of adjustability to suit hands of different sizes. It is intended that the device 10 be made in various sizes, with each size having the affixed stretchable straps 30, 32 of different length as compared to another size, so as to accommodate different ranges of minimum and maximum sizes of hands.

The modifications shown in FIGS. 4-9 also included a variation of the digit-supporting therapeutic device for a hand of the invention in which the device 10 is provided with an elongated main body portion 40 having a tubular section 40' serving as a wrist support section. Extending from an upper edge surface of this wrist support section is a connecting flap or section 44. In this embodiment, a doubled-over portion or sleeve section 42 is formed integrally with the connecting flap to define the thumb-sleeve 12 in which the thumb is inserted as best seen in FIGS. 5A and 6. The finger-sleeves 14 and 16 are a separate element attachable to the thumb-sleeve by the length-adjustable straps 20, 22 described above with hook-and-pile fasteners elements, as seen in FIG. 5B, and as described above, with the thumb-sleeve also having a first hook-and-pile fastener portion for removably securing the ends of the straps 20,22, as described above. It is noted that the thumb-sleeve 12 formed integrally with the connecting flap has its opening facing downwardly toward the wrist support section 40', so that as the hand is inserted through the tubular wrist section 40', after having positioned the wrist support about the wrist, the thumb of the hand immediately is juxtapositioned at the opening of the thumb-sleeve for sliding entry therein as the device is pulled on.

Figure 7:
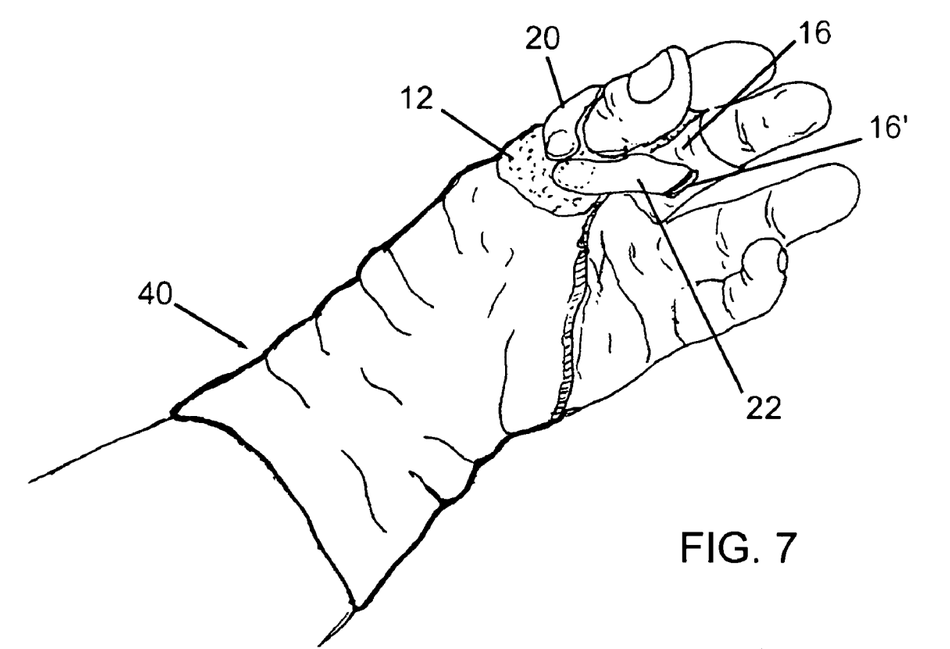
FIG. 7 is a front isometric view of a modification of device of FIG. 4 shown worn on a hand.
Figure 8:
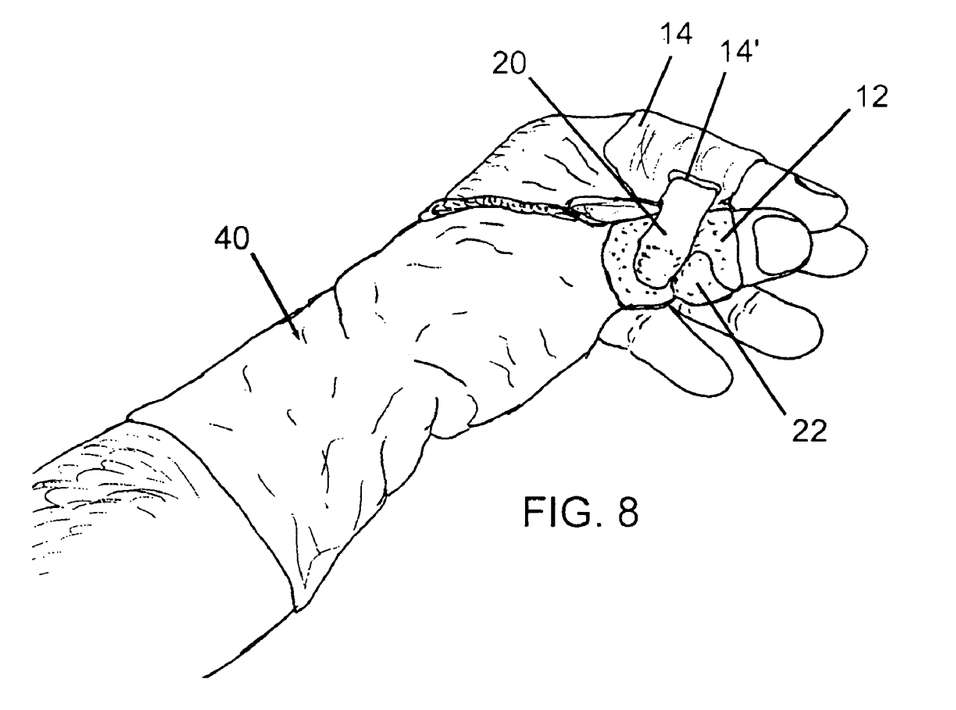
FIG. 8 is a rear isometric view thereof and shown worn on a hand.
Figure 9:
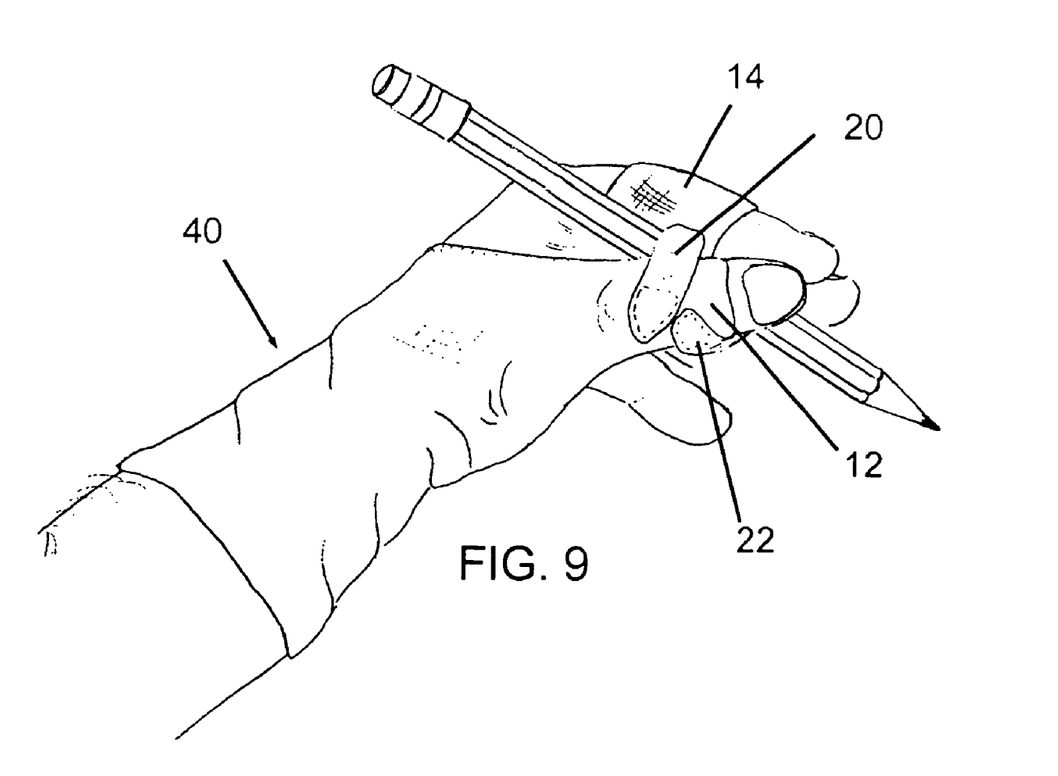
FIG. 9 is a view similar to FIG. 7 but showing the hand grasping and holding a pencil for writing therewith by means of the support to the thumb, forefinger and index finger provided by the digit-supporting therapeutic device of the invention.

It is noted that, whereas in FIG. 4 each of the straps 20, 22 is shown as having one end permanently affixed to the thumb-sleeve, as described above, the modification shown in FIGS. 7-9 allows the end of each strap 20,22 to be removably attached to the thumb-sleeve via mating hook-and-pile fastener elements. In this modification, the interior, or inner, surface of each strap 20, 22 is provided with the first half or portion of the hook-and-pile fastener, while the inner or interior surface of each end 20", 22" of the straps 20, 22 is provided with the second half or portion of the hook-and-pile fastener for varying or adjusting the effective length of each sleeve 20, 22. In addition, in this modification, the portion 12' of the thumb-sleeve 12 that has the second half or portion of the hook-and-pile fastener extends over a larger surface area of the thumb-sleeve, as best seen in FIGS. 7 and 8.

Figure 11:
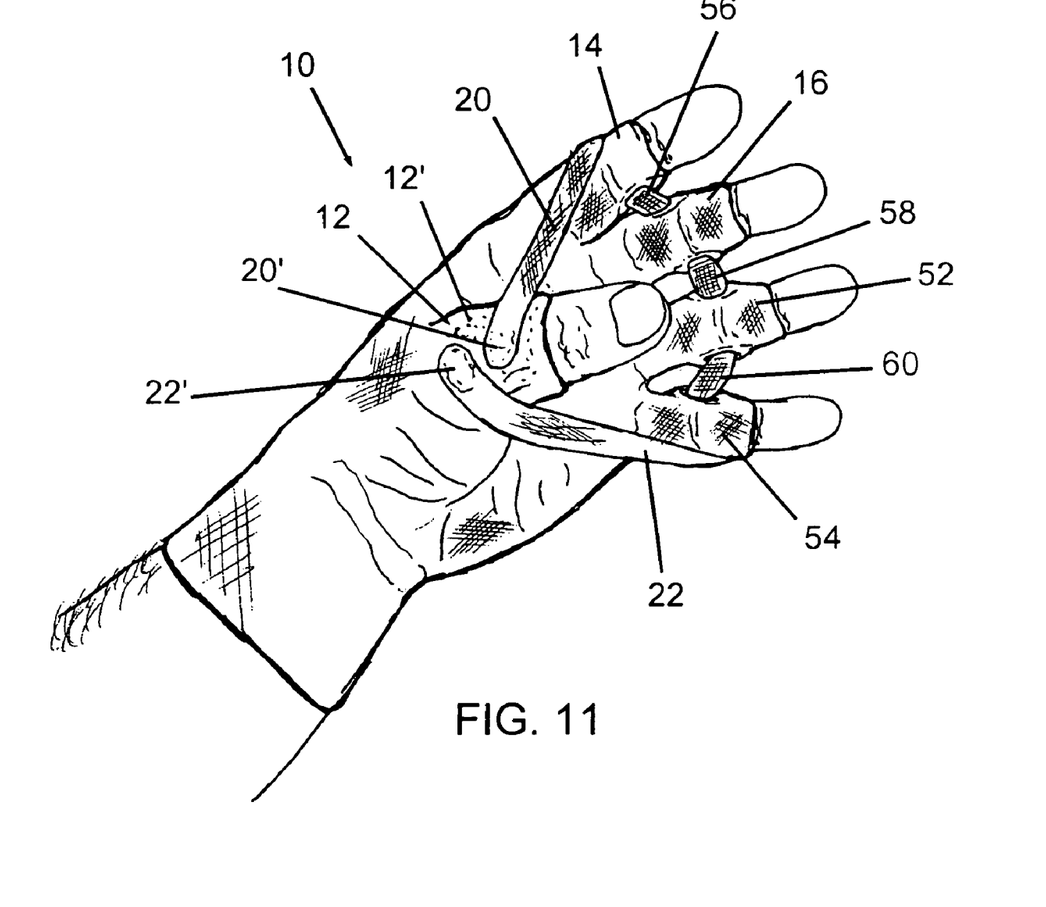
FIG. 11 is a front isometric view of another embodiment of the invention in which there are provided finger-sleeves for all four fingers besides a thumb-sleeve in which the finger-sleeves are interconnected by flexible and stretchable straps or bands with the length-adjustable straps for connecting the thumb-sleeve to the first and finger-sleeves.

Referring to FIG. 11, there is shown another embodiment configured as an integral glove 10', where there are also provided two additional finger-sleeves 52, 54 for the last two fingers of the hand. In this embodiment, the straps 20, 22 with the first part of hook-and-pile fastener elements are connected between the index-finger sleeve 16 and the pinkie-sleeve 54. Bands 56, 58 and 60 interconnect the last three finger sleeves 14, 52 and 54. These bands may or may not be stretchable. The straps 20, 22 may be also be inserted through slits or openings in the finger-sleeves 16 and 54 for varying the effective length of the straps, in the manner described above with reference to the first embodiment.

Figure 12:
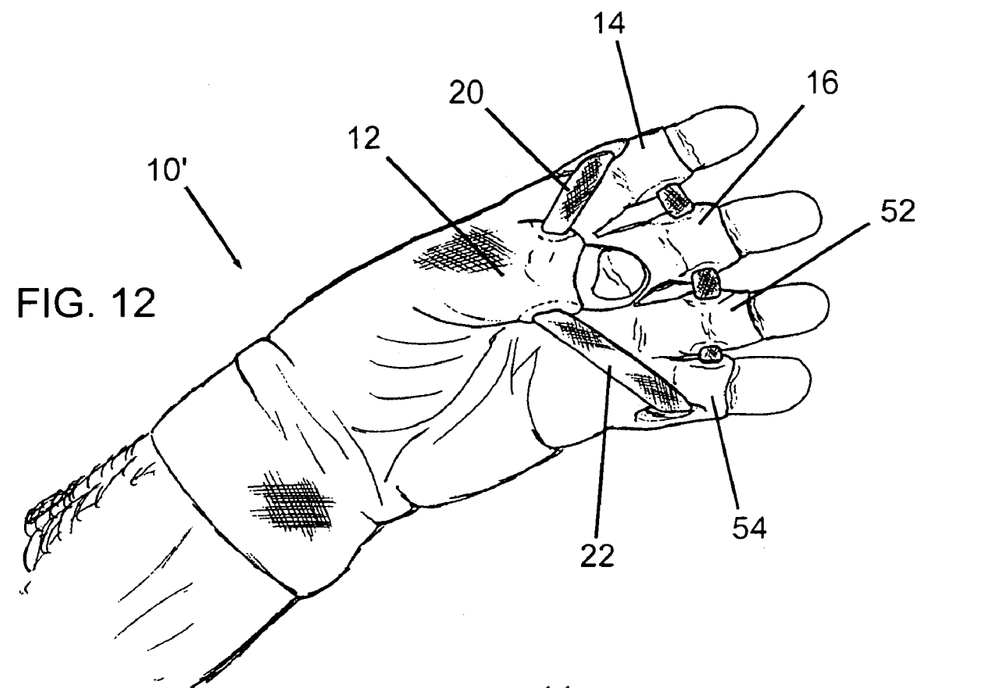
FIG. 12 is a front isometric view similar to the embodiment of FIG. 11, but where the forefinger sleeve and pinky-sleeve are connectable to the thumb-sleeve by means of stretchable straps or bands.

FIG. 12 shows a modification of the glove version of FIG. 11, in which the straps 20, 22 are stretchable and fixedly connected between the thumb-sleeve 12 and the finger-sleeves 14 and 54, respectively, in the manner also described above with respect to the first embodiment.

Figure 1:
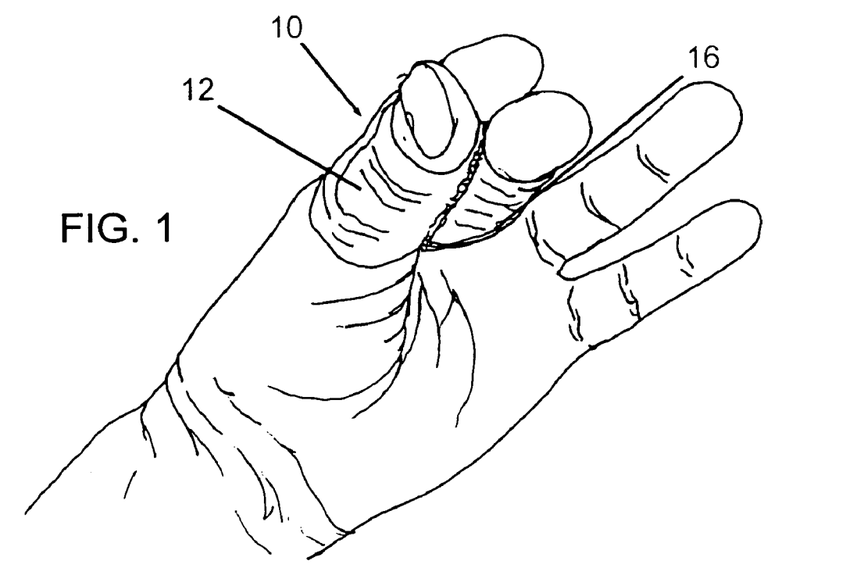
FIG. 1 is a front isometric view of the first embodiment of the digit-supporting therapeutic device for the fingers of a hand according to the invention shown worn on the thumb, index and middle fingers of a hand.
Figure 2:
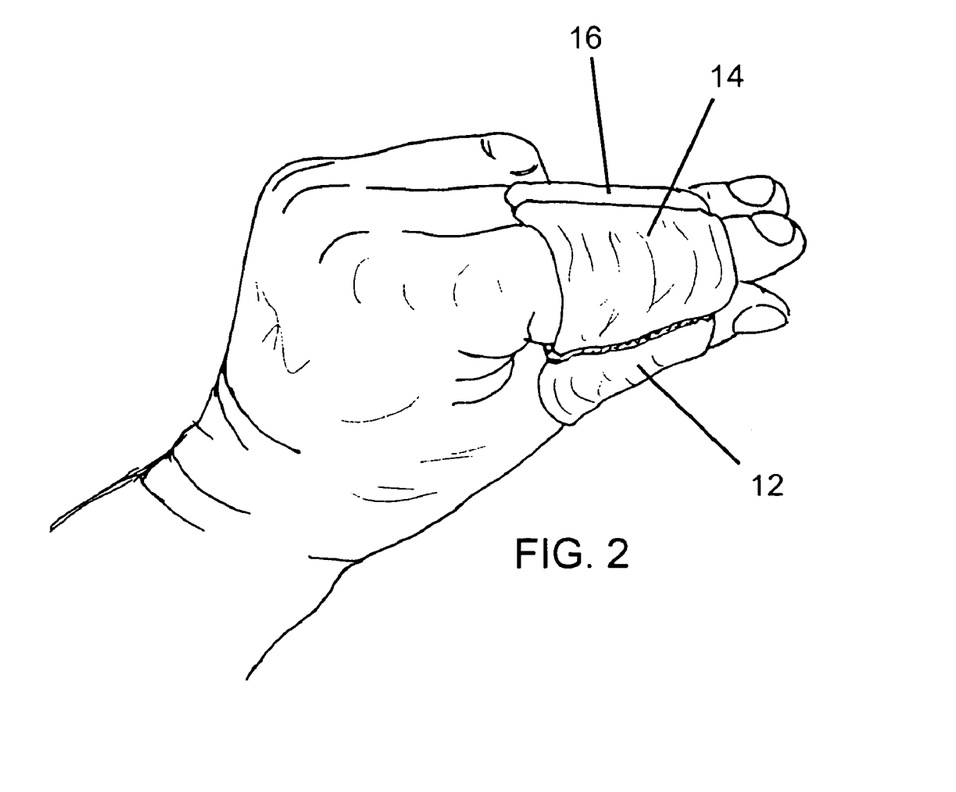
FIG. 2 is a rear isometric view of embodiment of FIG. 1.
Figure 13:
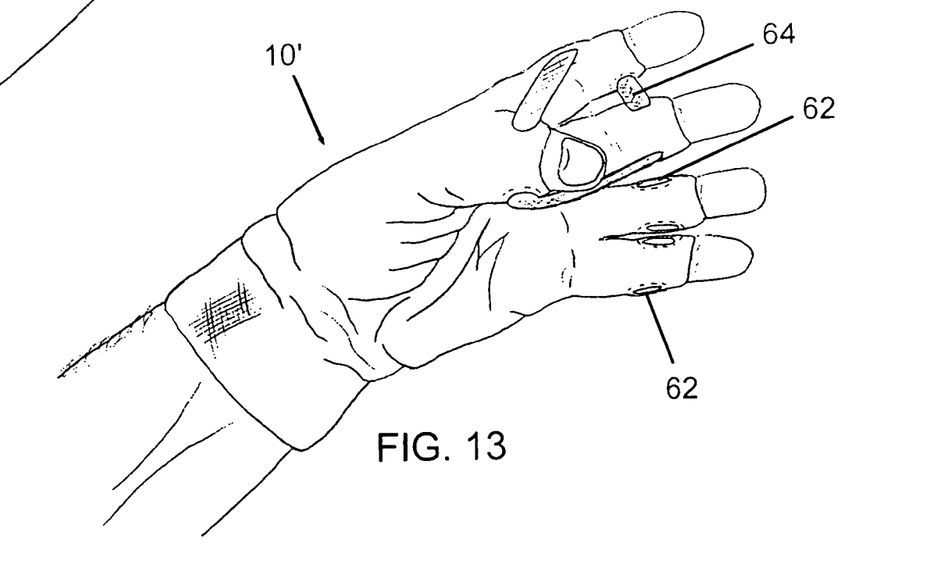
FIG. 13 is a front isometric view similar to the embodiment of FIG. 11, but where the two outer finger-sleeves are free and disconnected from other sleeves.

FIG. 13 shows yet another embodiment similar to FIGS. 12 and 13, but where the strap 22 is connected to the middle-finger sleeve as in the first preferred embodiment of FIG. 1, but where there are also provided two additional finger-sleeves 52, 54 that are not interconnected to the other main sleeves. This version provides greater flexibility to the hand than that of FIG. 12. It is also noted that in this version, the ends of the straps 20, 22 may be connected to the finger-sleeves by means slits or openings 62 similar to the slits 14', 16' of the first embodiment, whereby the strap 22 may be alternatively connected to any of the last three finger-sleeves 16, 52 or 54.

Figure 14:
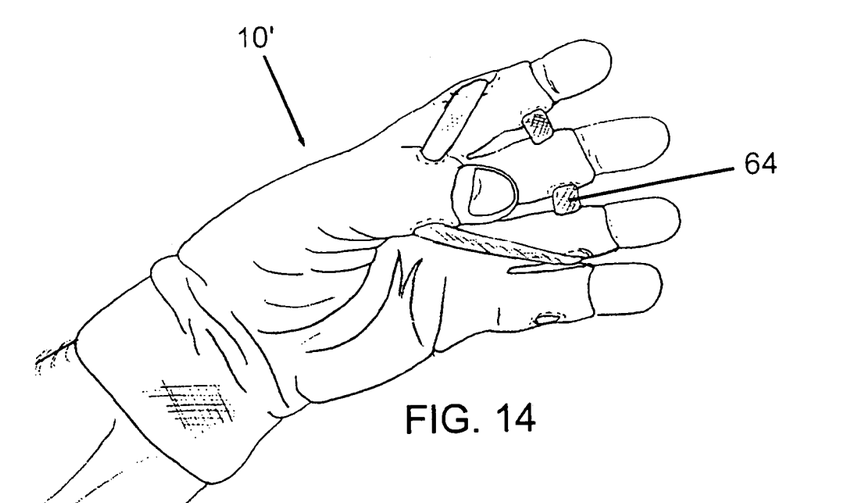
FIG. 14 is a front isometric view similar to the embodiment of FIG. 11, but where the pinky-sleeve is disconnected from the other sleeves.

FIG. 14 shows yet another embodiment similar to FIG. 13, but where the strap 22 is connected to the third-finger sleeve 52 and the finger-sleeves 16 and 52 are interconnected by a stretchable band 64.

Figure 15:
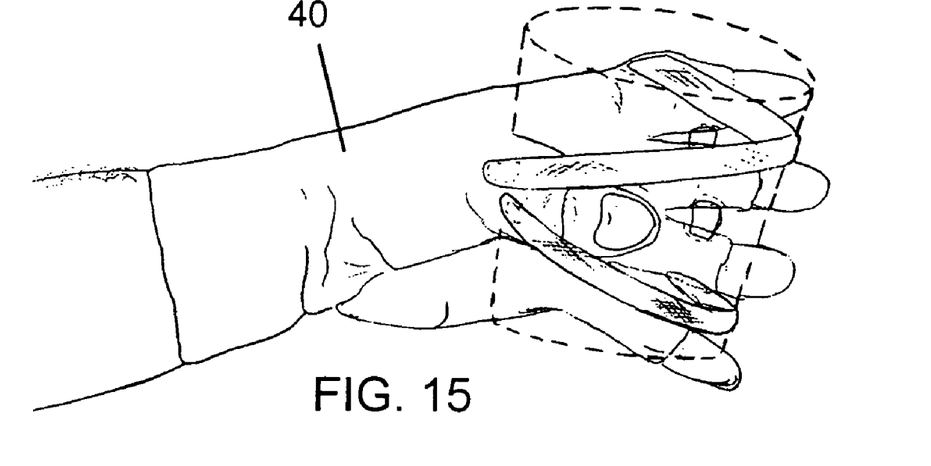
FIG. 15 is an isometric view showing the device of FIG. 14 in use for holding a glass.

Each of the versions of FIGS. 11-14 is used when larger objects are to be held and supported in the hand, such as a glass, as depicted in FIG. 15.

Each of the glove-versions of FIGS. 11-14 is also suitable for use by surgeons or dentists whose fine motor skill is of great importance, in order to provide additional steadying support to their hand or hands. Moreover, developmental hand skills, such as writing and scissor-use, is facilitated by use of the invention, as the desired functional skills patterns are facilitated. Musicians' hand skill may also facilitated by aiding in the holding of a violin bow or a guitar pick, and hobbyists who use small hand tools, may be assisted. The glove-version of the invention is also helpful to golfers in order to assist them in maintaining a perfect golf-club grip. Similarly, tennis and racketball players will be assisted in maintaining a perfect racket grip. The glove-version is also useful to assist people in holding onto a cane or walker.

The preferred embodiment with or without the wrist support, and the glove version, provide gradable or adjustable support to the fingers of the hand while allowing the performance of fine motor skills activities, such as writing, turning a nut or bolt, knitting crochet, needlepoint, picking up small objects such as coins, pills, buttons, paper clips, etc. They help hold and stabilize an object, thus allowing reduced muscle force to be required to manipulate that object. With the ability to assist the fingers of the hand to exert less muscle force during tool use, the support of the invention helps to limit wear and tear on hand, wrist and finger structures, thereby reducing the occurrence and severity of injury to these structures during work and leisure activities. Problems that are reduced include: Carpel tunnel syndrome, arthritis, tendonitis, pain, and other repetitive stress disorders. Use of the invention will also facilitate persons to return to work faster from injury, and use less hand-strength, by allowing fine motor skills to be used. The invention allows tasks to be performed requiring good hand strength and skill, and is an aid to persons who suffer from such conditions as, carpal tunnel syndrome, multiple sclerosis, arthritis, tendonitis, fractures, stroke, brain injury, diabetic neuropathy, pain and repetitive stress disorders, and many other neurological and orthopedic problems.

It is also noted that the present invention also envisions a modification where the there is no interconnection between the two finger-sleeves 14 and 16. In addition, other equivalent cooperating fasteners besides hook-and-pile may be used. Moreover, a version similar to FIG. 3 may be provided that is provided with a third finger-sleeve or with third and fourth finger-sleeves, in the manner of the embodiments of FIGS. 11-14, but without the wrist-support section and extension.

While specific embodiments of the invention have been shown and described, it is to be understood that numerous changes and modifications may be made therein without departing from the scope and spirit of the invention as set forth in the appended claims.

The invention claimed is:

1. A therapeutic hand device comprising:
a first thumb-sleeve for receiving therein the thumb of a hand, a second index-finger sleeve for receiving therein the index finger of the hand, and a third middle-finger sleeve for receiving therein the middle finger of the hand; means for directly connecting together said first thumb-sleeve with said second sleeve and for directly connecting together said first thumb-sleeve with said third sleeve to form an interior hollow volume between said first, second and third sleeves for placing said thumb sleeve in opposition to said second and third sleeves, whereby an object may be inserted into said interior hollow volume between said first, second and third sleeves, so that when said first, second and third sleeves are placed respectively on the thumb, index finger and middle finger of the hand, said thumb and fingers may hold and manipulate the object with support and assistance by said sleeves;
each said sleeve comprising a first connecting portion and a second connecting portion; said means for connecting together comprising means for connecting together said first, second and third sleeves and comprises first connecting means connected between said first connecting portions of said first sleeve and said second sleeve, second connecting means connected between said second connecting portions of said first sleeve and said third sleeve, and third connecting means connected between said second connecting portion of said second sleeve and said first connecting portion of said third sleeve.

2. The therapeutic hand device according to claim 1, wherein each of said sleeves is made of a flexible, stretchable material; said flexible, stretchable material providing a variable biasing force as said second and third sleeves are separated from said first sleeve when worn on a hand in order to hold and manipulate an object in said open space.

3. The therapeutic hand device according to claim 1, wherein each of said first and second connecting means comprises a length-adjustable connector in order to vary the distance of separation between said first and second sleeves, and the distance between said first and third sleeves, respectively.

4. The therapeutic hand device according to claim 3, wherein said third connecting means fixedly connects said second and third sleeves together for relatively fixed spacing therebetween.

5. The therapeutic hand device according to claim 3, wherein each of said length-adjustable connectors comprises an elongated band element having a first end, a second end, an inner surface and an outer surface; one of said inner surface and outer surface having a first cooperating section of a fastening means; and at least one of said first and second ends having a second cooperating section of the fastening means, whereby said second cooperating means is adjustably and removably fastenable to different portions of said first cooperating section for varying the effective length of the respective said band element for varying the distance between said first sleeve and a respective said second and third sleeve.

6. The therapeutic hand device according to claim 3, wherein each of said length-adjustable connectors comprises an elongated band element having a first end connected to a respective said second and third sleeve, a second end, an inner surface and an outer surface; at least one of said inner surface, said outer surface, and said second end having a first cooperating section of a fastening means; said first sleeve comprising a second cooperating section of the fastening means, whereby said second cooperating means is adjustably and removably fastenable to different portions of said first cooperating section for varying the effective length of the respective said band element for varying the distance between said first sleeve and a respective said second and third sleeve.

7. The therapeutic hand device according to claim 1, further comprising a wrist support section for supporting the wrist of the hand, and an extension portion connected to said wrist support section; said first sleeve being formed integrally with said wrist support section by means of said extension portion; said means for connecting together said first sleeve with said second sleeve and said first sleeve with said third sleeve comprising a first and a second elongated band element, respectively, each having an inner surface and an outer surface; at least a portion of at least one of said inner surface and outer surface having a first cooperating section of a fastening means; said first sleeve having a second cooperating section of the fastening means, whereby said first and second band elements connect said second and third sleeves to said first sleeve.

8. A therapeutic hand device comprising:
a first thumb-sleeve for receiving therein the thumb of a hand, a second finger sleeve for receiving therein the finger of the hand, and at least one additional finger-sleeve; means for directly connecting together said first sleeve with said second sleeve and for directly connecting together said first sleeve with said at least one additional finger-sleeve for placing said thumb sleeve in opposition to said other sleeves; said first, second, and at least one additional finger sleeves forming an interior hollow volume therebetween, whereby an object may be inserted between said sleeves, so that when said sleeves are placed respectively on the thumb and fingers of the hand, said thumb and fingers may hold and manipulate the object with support and assistance by said sleeves;
said means for connecting together comprising first strap means connected between said first sleeve and said second sleeve, and second strap means connected between said first sleeve and said at least one additional finger-sleeve.

9. The therapeutic hand device according to claim 8, wherein each of said first and second strap means comprises a length-adjustable connector.

10. A method of using a therapeutic device for the fingers of a hand, which therapeutic device comprises at least two finger sleeves for receiving therein at least two fingers of a hand, means for connecting together the at least two sleeves with each other and for placing the at least two finger sleeves in opposition to the thumb of a hand; the at least two sleeves in combination with the thumb forming an interior hollow volume therebetween, said method comprising:
   (a) attaching the at least two sleeves to at least two digits of a hand such that the thumb is held in opposition to the at least two digits and increasing the distance between the thumb relative to the at least two digits inserted in the at least two sleeves;
   (b) inserting an object in said interior hollow volume;
   (c) decreasing the distance between the thumb relative to the at least two digits inserted in the at least two sleeves for grasping the object inserted in said interior hollow volume by the thumb and the at least two fingers of the hand; and
   (d) supporting said thumb and said at least two finger sleeves in the position of said step (c) by said means for connecting together, whereby the thumb and at least some of the other fingers of the hand are supported in their pinching grasp of the object of said step (b).

11. A therapeutic hand device comprising:
a first thumb-sleeve for receiving therein the thumb of a hand, a second index-finger sleeve for receiving therein the index finger of the hand, and a third middle-finger sleeve for receiving therein the middle finger of the hand; means for directly connecting together said first thumb-sleeve with said second sleeve and for directly connecting together said first thumb-sleeve with said third sleeve to form an interior hollow volume between said first, second and third sleeves for placing said thumb sleeve in opposition to said second and third sleeves, whereby an object may be inserted into said interior hollow volume between said first, second and third sleeves, so that when said first, second and third sleeves are placed respectively on the thumb, index finger and middle finger of the hand, said thumb and fingers may hold and manipulate the object with support and assistance by said sleeves;
said means for connecting together said first sleeve with said second sleeve and said first sleeve with said third sleeve comprising a first and a second elongated band element each having a first end, a second end, an inner surface and an outer surface; one of said inner surface and outer surface having a first cooperating section of a fastening means; said first sleeve having a second cooperating section of the fastening means, whereby the distance between said first sleeve and said second sleeve, and the distance between said first sleeve and said third sleeve may be adjusted via said first elongated band and said second elongated band, respectively, for adjusting said hollow interior volume in which an object is placed.

12. A therapeutic hand device comprising:
a first thumb-sleeve for receiving therein the thumb of a hand, a second index-finger sleeve for receiving therein the index finger of the hand, and a third middle-finger sleeve for receiving therein the middle finger of the hand; means for directly connecting together said first thumb-sleeve with said second sleeve and for directly connecting together said first thumb-sleeve with said third sleeve to form an interior hollow volume between said first, second and third sleeves for placing said thumb sleeve in opposition to said second and third sleeves, whereby an object may be inserted into said interior hollow volume between said first, second and third sleeves, so that when said first, second and third sleeves are placed respectively on the thumb, index finger and middle finger of the hand, said thumb and fingers may hold and manipulate the object with support and assistance by said sleeves;
a wrist support section for supporting the wrist of the hand, and an extension portion connected to said wrist support section; said first sleeve being formed integrally with said wrist support section by means of said extension portion; said means for connecting together said first sleeve with said second sleeve and said first sleeve with said third sleeve comprising a first and a second elongated band element, respectively, each having an inner surface and an outer surface; at least a portion of at least one of said inner surface and outer surface having a first cooperating section of a fastening means; said first sleeve having a second cooperating section of the fastening means, whereby said first and second band elements connect said second and third sleeves to said first sleeve.

13. The therapeutic hand device according to claim 12, further comprising at least one additional finger-sleeve connected to at least one of said third sleeve and said extension portion.

14. The therapeutic hand device according to claim 13, comprising two additional finger-sleeves for the fourth and fifth fingers of the hand; said means for connecting connecting said fourth finger-sleeve to said third finger-sleeve and said fifth finger-sleeve to said fourth finger-sleeve.

* * * * *